United States Patent [19]

Iwasaki et al.

[11] Patent Number: 6,100,374
[45] Date of Patent: Aug. 8, 2000

[54] METHOD OF PURIFYING CRUDE NAPHTHALENEDICARBOXLIC ACID AND PROCESS FOR PREPARING POLYETHYLENE NAPHTHALATE

[75] Inventors: Hiroshi Iwasaki, Kuga-gun; Satoshi Inoki, Kugá-gun; Hiromi Ueki, Kuga-gun, all of Japan

[73] Assignee: Mitsui Chemicals Inc., Tokyo, Japan

[21] Appl. No.: 09/254,439

[22] PCT Filed: Sep. 5, 1997

[86] PCT No.: PCT/JP97/03129

§ 371 Date: Mar. 9, 1999

§ 102(e) Date: Mar. 9, 1999

[87] PCT Pub. No.: WO98/11047

PCT Pub. Date: Mar. 19, 1998

[30] Foreign Application Priority Data

Sep. 10, 1996 [JP] Japan ................................... 8-239391
Sep. 10, 1996 [JP] Japan ................................... 8-239392

[51] Int. Cl.$^7$ ........................................................ C08F 6/00
[52] U.S. Cl. ...................... 528/483; 528/272; 528/275; 528/298; 528/487; 528/456; 528/502; 528/503; 526/71; 560/79; 560/80; 560/91; 560/93; 560/94; 560/99
[58] Field of Search ..................... 528/272, 275, 528/298, 483, 487, 496, 502, 503; 526/71, 79; 560/80, 91, 93, 94, 99

[56] References Cited

U.S. PATENT DOCUMENTS 3,632,856  1/1972  Hollstein .
4,745,211  5/1988  Jackson, Jr. et al. ..................... 560/80

FOREIGN PATENT DOCUMENTS 7173100  7/1995  Japan .

WO92/21645  12/1992  WIPO .

Primary Examiner—Samuel A. Acquah

[57] ABSTRACT

The process for preparing polyethylene naphthalate according to the invention is intended to obtain polyethylene naphthalate having a low impurity content from naphthalenedicarboxylic acid containing impurities. This process comprises the steps of: mixing crude naphthalenedicarboxylic acid and an ethylene glycol aqueous solution, heating the resulting mixture to esterify a part of the naphthalenedicarboxylic acid and thereby give a naphthalenedicarboxylic acid ester and dissolving the naphthalenedicarboxylic acid ester in the ethylene glycol aqueous solution; then contacting impurities, which are contained in the crude naphthalenedicarboxylic acid and capable of being hydrogenated, with hydrogen in the presence of a hydrogenation catalyst to hydrogenate the impurities and dissolving the hydrogenated impurities in the ethylene glycol aqueous solution; and subsequently crystallizing the naphthalenedicarboxylic acid ester, separating the resulting crystals from the ethylene glycol aqueous solution and polycondensing the resulting naphthalenedicarboxylic acid ester. The method of purifying crude naphthalenedicarboxylic acid is intended to obtain naphthalenedicarboxylic acid and a naphthalenedicarboxylic acid ester having a low content of aldehydes from naphthalenedicarboxylic acid containing aldehydes. This method comprises the steps of: mixing crude naphthalenedicarboxylic acid and an alcohol aqueous solution, heating the resulting mixture to esterify a part of the naphthalenedicarboxylic acid and thereby give a naphthalenedicarboxylic acid ester and dissolving the naphthalenedicarboxylic acid ester in the alcohol aqueous solution; then contacting aldehydes, which are contained in the crude naphthalenedicarboxylic acid, with a sulfite to give aldehyde adducts and dissolving the aldehyde adducts in the alcohol aqueous solution; and subsequently crystallizing the naphthalenedicarboxylic acid and the naphthalenedicarboxylic acid ester and separating them from the alcohol aqueous solution.

9 Claims, No Drawings

METHOD OF PURIFYING CRUDE NAPHTHALENEDICARBOXLIC ACID AND PROCESS FOR PREPARING POLYETHYLENE NAPHTHALATE

This application is the National Phase entry under 35 USC 371 of PCT/JP97/03129, filed Sep. 5, 1997.

TECHNICAL FIELD

The present invention relates to a method of purifying crude naphthalenedicarboxylic acid by which a mixture of naphthalenedicarboxylic acid and naphthalenedicarboxylic acid ester having a low impurity content or high-purity naphthalenedicarboxylic acid can be obtained from naphthalenedicarboxylic acid containing impurities, and also relates to a process for preparing polyethylene naphthalate by which polyethylene naphthalate having a low impurity content can be obtained.

BACKGROUND ART

Naphthalenedicarboxylic acid is prepared by, for example, oxidizing dialkylnaphthalene in the presence of cobalt, manganese and bromine. The naphthalenedicarboxylic acid prepared by the process, however, contains, as impurities, trimellitic acid and aldehydes produced as by-products during the course of the preparation or cobalt, manganese and bromine derived from a catalyst. If the impurity-containing naphthalenedicarboxylic acid (crude naphthalenedicarboxylic acid) is used as a starting material for preparing polyethylene naphthalate, the resulting polyethylene naphthalate is occasionally colored, or mold staining may take place in the molding process to decrease transparency of the molded products, resulting in lowering of product quality. In order to obtain high-quality polyethylene naphthalate, therefore, the crude naphthalenedicarboxylic acid needs to be purified before it is used as a starting material for preparing polyethylene naphthalate.

Japanese Patent Laid-Open Publication No. 110650/1989 describes a method of purifying crude naphthalenedicarboxylic acid comprising the steps of: causing impure 2,6-naphthalenedicarboxylic acid to react with ethylene glycol in an amount of at least 2 mol based on 1 mol of the 2,6-naphthalenedicarboxylic acid in the presence of catalytic amounts of tertiary amine and a titanium-containing compound to prepare bis(2-hydroxyethyl) 2,6-naphthalenedicarboxylate; crystallizing the bis(2-hydroxyethyl) 2,6-naphthalenedicarboxylate; and recovering the purified bis(2-hydroxyethyl) 2,6-naphthalenedicarboxylate.

National Publication of International Patent No. 508870/1993 describes a process for preparing purified dimethyl naphthalenedicarboxylate comprising the steps of: causing 2,6-naphthalenedicarboxylic acid to react with methanol in an appropriate reaction region to prepare a reaction mixture containing dissolved dimethyl 2,6-naphthalenedicarboxylate and monomethyl 2,6-naphthalenedicarboxylate; cooling the reaction mixture to a temperature of not higher than about 40° C. to crystallize major parts of the dissolved dimethyl 2,6-naphthalenedicarboxylate and monomethyl 2,6-naphthalenedicarboxylate; fractionating the thus crystallized dimethyl 2,6-naphthalenedicarboxylate and monomethyl 2,6-naphthalenedicarboxylate from the reaction mixture solution; heating the thus fractionated dimethyl 2,6-naphthalenedicarboxylate and monomethyl 2,6-naphthalenedicarboxylate in a recrystallization solvent to a temperature high enough for dissolving at least a part of the dimethyl 2,6-naphthalenedicarboxylate and substantially all of the monomethyl 2,6-naphthalenedicarboxylate; recrystallizing the dimethyl 2,6-naphthalenedicarboxylate, which has been dissolved in the recrystallization solvent, at a temperature at which a major part of the monomethyl 2,6-naphthalenedicarboxylate is held in the recrystallization mother liquor; and fractionating the thus recrystallized dimethyl 2,6-naphthalenedicarboxylate from the recrystallization mother liquor.

Japanese Patent Laid-Open Publication No. 173100/1995 describes a process for preparing high-purity 2,6-naphthalenedicarboxylic acid comprising the steps of: dissolving coarse crystals of impurity-containing 2,6-naphthalenedicarboxylic acid in water in a supercritical or subcritical state; cooling the resulting solution at a temperature of not higher than 300° C. to precipitate crystals; and separating the crystals from the mother liquor at a temperature of 100 to 300° C.

In the circumstances, eagerly desired are development of a method of purifying crude naphthalenedicarboxylic acid by which the impurity content can be decreased through easier operations and development of a process for preparing polyethylene naphthalate by which polyethylene naphthalate having a lower impurity content and almost free from being colored or occurrence of mold staining can be obtained through easier operations.

The present invention has been made in view of the prior art as mentioned above, and it is an object of the invention to provide a method of purifying crude naphthalenedicarboxylic acid, by which a mixture of naphthalenedicarboxylic acid and a naphthalenedicarboxylic acid ester having a low impurity content or high-purity naphthalenedicarboxylic acid can be obtained. It is another object of the invention to provide a process for preparing polyethylene naphthalate, by which polyethylene naphthalate having a low impurity content and almost free from being colored or occurrence of mold staining can be obtained from naphthalenedicarboxylic acid containing impurities.

DISCLOSURE OF THE INVENTION

The process for preparing polyethylene naphthalate according to the present invention comprises the steps of:

mixing crude naphthalenedicarboxylic acid and an ethylene glycol aqueous solution, heating the resulting mixture to esterify a part of the naphthalenedicarboxylic acid and thereby give a naphthalenedicarboxylic acid ester and dissolving the naphthalenedicarboxylic acid ester in the ethylene glycol aqueous solution;

then contacting impurities, which are contained in the crude naphthalenedicarboxylic acid and capable of being hydrogenated, with hydrogen in the presence of a hydrogenation catalyst to hydrogenate the impurities and dissolving the hydrogenated impurities in the ethylene glycol aqueous solution; and subsequently crystallizing the naphthalenedicarboxylic acid ester, separating the resulting crystals from the ethylene glycol aqueous solution and polycondensing the resulting naphthalenedicarboxylic acid ester.

In the present invention, the ethylene glycol aqueous solution for esterifying the crude naphthalenedicarboxylic acid preferably has an ethylene glycol concentration of 20 to 95% by weight based on 100% by weight of the total of water and ethylene glycol.

The polyethylene naphthalate obtained by the process of the invention has high transparency and is suitably used as a material for producing various molded articles.

The method of purifying crude naphthalenedicarboxylic acid according to the present invention comprises the steps of:

mixing crude naphthalenedicarboxylic acid and an alcohol aqueous solution, heating the resulting mixture to esterify a part of the naphthalenedicarboxylic acid and thereby give a naphthalenedicarboxylic acid ester and dissolving the naphthalenedicarboxylic acid ester in the alcohol aqueous solution;

then contacting aldehydes, which are contained in the crude naphthalenedicarboxylic acid, with a sulfite to give aldehyde adducts and dissolving the aldehyde adducts in the alcohol aqueous solution; and subsequently crystallizing the naphthalenedicarboxylic acid and the naphthalenedicarboxylic acid ester and separating them from the alcohol aqueous solution.

According to the method of the invention, high-purity naphthalenedicarboxylic acid and naphthalene dicarboxylic acid ester are obtained from crude naphthalenedicarboxylic acid. If ethylene glycol is used as the alcohol in the above method and if the naphthalenedicarboxylic acid ester obtained by the method is polycondensed, polyethylene naphthalate having a low impurity content can be obtained.

Another embodiment of the method of purifying crude naphthalenedicarboxylic acid according to the present invention comprises the steps of:

mixing crude naphthalenedicarboxylic acid and an alcohol aqueous solution, heating the resulting mixture to esterify a part of the naphthalenedicarboxylic acid and thereby give a naphthalenedicarboxylic acid ester and dissolving the naphthalenedicarboxylic acid ester in the alcohol aqueous solution;

then contacting aldehydes, which are contained in the crude naphthalenedicarboxylic acid, with a sulfite to give aldehyde adducts and dissolving the aldehyde adducts in the alcohol aqueous solution; and subsequently lowering the alcohol concentration of the alcohol aqueous solution to hydrolyze the naphthalenedicarboxylic acid ester and recovering the naphthalenedicarboxylic acid.

The alcohol used in the method of purifying crude naphthalenedicarboxylic acid according to the invention is preferably methanol, ethanol or ethylene glycol.

According to the method of the invention, high-purity naphthalenedicarboxylic acid can be obtained from crude naphthalenedicarboxylic acid. The high-purity naphthalenedicarboxylic acid can be suitably used as a starting material for preparing polyethylene naphthalate.

BEST MODE FOR CARRYING OUT THE INVENTION

The process for preparing polyethylene naphthalate is described below in detail.

In the first place, crude naphthalenedicarboxylic acid and an ethylene glycol aqueous solution are mixed, and a part of the naphthalenedicarboxylic acid is esterified to give a naphthalenedicarboxylic acid ester. The resulting naphthalenedicarboxylic acid ester is dissolved in the ethylene glycol aqueous solution.

The crude naphthalenedicarboxylic acid is prepared by, for example, oxidizing dialkylnaphthalene in the presence of cobalt, manganese and bromine. In the crude naphthalenedicarboxylic acid, impurities which are produced as by-products during the course of the preparation and are capable of being hydrogenated, such as trimellitic acid, and 6-formyl-2-naphthoic acid, and cobalt, manganese and bromine which are derived from the catalyst are contained in amounts of usually several hundreds to several thousands ppm.

The crude naphthalenedicarboxylic acid is used in an amount of 0.007 to 0.5 mol, preferably 0.03 to 0.10 mol, based on 1 mol of ethylene glycol in the ethylene glycol aqueous solution. The ethylene glycol concentration of the ethylene glycol aqueous solution is in the range of 20 to 95% by weight, preferably 40 to 90% by weight, more preferably 60 to 80% by weight, based on 100% by weight of the total of water and ethylene glycol.

The esterification of the naphthalenedicarboxylic acid is carried out under a pressure of usually 2 to 80 kg/cm$^2$, preferably 10 to 50 kg/cm$^2$, at a temperature of usually 200 to 300° C., preferably 160 to 280° C., for a period of usually 0.2 to 6 hours, preferably 1 to 4 hours. The esterification ratio of the naphthalenedicarboxylic acid depends on the ethylene glycol concentration of the ethylene glycol aqueous solution, etc., but it is usually 20 to 90%, preferably 40 to 70%.

The esterification ratio is defined by the following equation.

$$\text{The esterification ratio} = \frac{\text{Number of esterified carboxyl groups}}{\text{Number of all carboxyl groups before esterification}} \times 100$$

By the esterification reaction, a naphthalenedicarboxylic acid monoester (NDA-mEG) and a naphthalenedicarboxylic acid diester (NDA-dEG), each of which is an ester of the naphthalenedicarboxylic acid, are produced, and these naphthalenedicarboxylic acid monoester and naphthalenedicarboxylic acid diester are dissolved in the ethylene glycol aqueous solution.

In the next place, impurities, which are contained in the crude naphthalenedicarboxylic acid and capable of being hydrogenated, are contacted with hydrogen to hydrogenate the impurities capable of being hydrogenated.

The hydrogenation of the impurities capable of being hydrogenated is carried out under a pressure of usually 20 to 80 kg/cm$^2$, preferably 30 to 60 kg/cm$^2$, at a temperature of usually 160 to 300° C., preferably 200 to 280° C., for a period of usually 0.05 to 2.0 hours, preferably 0.1 to 1.0 hour. As the hydrogenation catalyst, any of hydrogenation catalysts hitherto known is employable. Examples of the hydrogenation catalysts include Fe, Co, Ni, Ru, Rh, Pd, Os, Ir and Pt. The hydrogenation catalyst is used in an amount of 0.0005 to 1% by weight, preferably 0.003 to 0.3% by weight, in terms of weight of a metal in the hydrogenation catalyst, based on the total weight of naphthalenedicarboxylic acid, ethylene glycol and water.

The impurities capable of being hydrogenated are hydrogenated, and as a result, they become compounds soluble in the ethylene glycol aqueous solution and are dissolved in the ethylene glycol aqueous solution.

In the present invention, the above step is followed by cooling the ethylene glycol aqueous solution to crystallize (precipitate) the naphthalenedicarboxylic acid and the naphthalenedicarboxylic acid ester. The precipitated naphthalenedicarboxylic acid and naphthalenedicarboxylic acid ester are separated from the ethylene glycol aqueous solution to obtain a mixture of the naphthalenedicarboxylic acid and the naphthalenedicarboxylic acid ester containing small amounts of impurities. In the mixture of the naphthalenedicarboxylic acid and the naphthalenedicarboxylic acid ester, the impurities are contained in amounts of usually not more than 100 ppm, preferably not more than 50 ppm.

The ratio between the naphthalenedicarboxylic acid and the naphthalenedicarboxylic acid ester obtained above can be controlled by adjusting the ethylene glycol concentration of the ethylene glycol aqueous solution and/or the temperature for the crystallization.

Then, the mixture of the naphthalenedicarboxylic acid and the naphthalenedicarboxylic acid ester is subjected to polycondensation reaction wherein ethylene glycol may be added to the mixture if needed.

The polycondensation reaction is conducted in accordance with a conventional method. That is, the mixture is heated to a temperature of not lower than the melting point of the resulting polyethylene naphthalate under reduced pressure in the presence of a polycondensation catalyst, while glycol eliminated during the reaction is distilled away from the system. The polycondensation reaction may be carried out in the presence of a stabilizer.

The polycondensation reaction is carried out under the conditions of a reaction temperature of usually 250 to 290° C., preferably 260 to 280° C., and a pressure of usually not more than 500 Torr, preferably not more than 200 Torr.

Examples of the polycondensation catalysts employable herein include germanium compounds, such as germanium dioxide, germanium tetraethoxide and germanium tetra-n-butoxide; antimony catalysts, such as antimony trioxide; and titanium compounds, such as titanium tetrabutoxide. The polycondensation catalyst is used in an amount of usually 0.0005 to 0.2% by weight, preferably 0.001 to 0.05% by weight, in terms of weight of a metal in the polycondensation catalyst, based on the total weight of the naphthalenedicarboxylic acid, the naphthalenedicarboxylic acid ester and ethylene glycol.

The polyethylene naphthalate prepared by the polycondensation reaction has an intrinsic viscosity [η], as measured in o-chlorophenol at 25° C., of usually 0.4 to 1.5 dl/g, and has a density of usually not less than 1.37 g/cm$^3$.

The polyethylene naphthalate obtained as above may be further subjected to:

a step of precrystallization wherein the polyethylene naphthalate is maintained in a dry state at a temperature of not lower than its temperature rise crystallization temperature and lower than its melting point, preferably at a temperature of higher than its temperature rise crystallization temperature by not less than 10° C. and lower than its melting point by not less than 40° C., for a period of 1 to 30 minutes, preferably 5 to 20 minutes; and a step of solid phase polycondensation wherein the polyethylene naphthalate is heated at a temperature of usually 190 to 230° C., preferably 195 to 225° C., under a pressure of usually 1 kg/cm$^2$-G to 10 Torr, preferably ordinary pressure to 100 Torr.

The polyethylene naphthalate obtained as above has a low impurity content and has good transparency.

Next, the method of purifying crude naphthalenedicarboxylic acid is described in detail.

In the first place, crude naphthalenedicarboxylic acid and an alcohol aqueous solution are mixed and heated to esterify a part of the naphthalenedicarboxylic acid and thereby give a naphthalenedicarboxylic acid ester, and the obtained naphthalenedicarboxylic acid ester is dissolved in the ethylene glycol aqueous solution.

The crude naphthalenedicarboxylic acid is used in an amount of usually 0.007 to 0.5 mol, preferably 0.03 to 0.10 mol, based on 1 mol of alcohol in the alcohol aqueous solution. The alcohol concentration of the alcohol aqueous solution is in the range of 20 to 95% by weight, preferably 40 to 90% by weight, more preferably 60 to 80% by weight.

The alcohol used in the alcohol aqueous solution is preferably an alcohol having 8 or less carbon atoms, and examples thereof include aliphatic alcohols, such as methanol, ethanol, propanol, isopropanol, butanol, pentanol, hexanol, heptanol and octanol; alicyclic alcohols, such as cyclohexanol; aromatic alcohols, such as phenol and benzyl alcohol; and dihydric alcohols, such as ethylene glycol. Of these, preferable are aliphatic alcohols and dihydric alcohols, and particularly preferable are methanol, ethanol and ethylene glycol.

The esterification of the naphthalenedicarboxylic acid is carried out under a pressure of usually 2 to 80 kg/cm$^2$, preferably 10 to 50 kg/cm$^2$, at a temperature of usually 200 to 300° C., preferably 160 to 280° C., for a period of usually 0.2 to 6 hours, preferably 1 to 4 hours. The esterification ratio of the naphthalenedicarboxylic acid depends on the alcohol concentration of the alcohol aqueous solution, etc., but it is usually 20 to 90% by weight, preferably 40 to 70% by weight.

By the esterification reaction, a naphthalenedicarboxylic acid monoester and a naphthalenedicarboxylic acid diester are produced, and these naphthalenedicarboxylic acid monoester and naphthalenedicarboxylic acid diester are dissolved in the alcohol aqueous solution.

In the next place, aldehydes, which are contained in the crude naphthalenedicarboxylic acid, are contacted with a sulfite. The sulfite is generally added by dissolving it in the reaction solution, e.g., alcohol aqueous solution, given after the esterification reaction, but it may be added to the alcohol aqueous solution prior to the esterification reaction.

Examples of the sulfites include metallic salts of hydrogensulfite, such as sodium hydrogensulfite and potassium hydrogensulfite.

The sulfite is used in an amount of usually 0.01 to 30% by weight, preferably 0.1 to 20% by weight, based on the alcohol aqueous solution.

The reaction of the aldehydes with the sulfite is carried out under a pressure of usually 0 to 80 kg/cm$^2$, preferably 2 to 50 kg/cm$^2$, at a temperature of usually 20 to 300° C., preferably 80 to 280° C., for a period of usually 0.05 to 5 hours, preferably 0.1 to 1.0 hour.

The aldehydes are contacted with the sulfite, and as a result, they become compounds soluble in the alcohol aqueous solution and are dissolved in the alcohol aqueous solution.

For example, 6-formyl-2-naphthoic acid becomes, by the reaction with sodium hydrogensulfite, the following compound which is soluble in the alcohol aqueous solution.

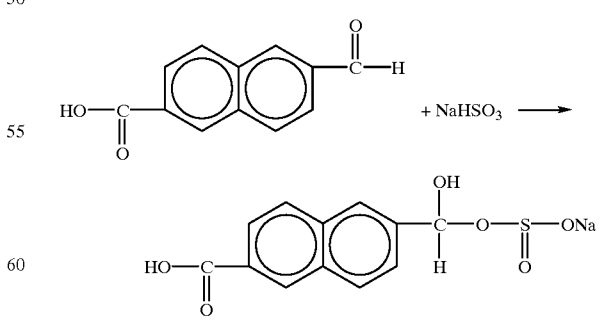

In the present invention, the above step is followed by cooling the resulting solution to crystallize (precipitate) the naphthalenedicarboxylic acid and the naphthalenedicarboxylic acid ester. The precipitated naphthalenedicarboxylic acid and naphthalenedicarboxylic acid ester are separated from the alcohol aqueous solution to obtain a mixture of the naphthalenedicarboxylic acid and the naphthalenedicarboxylic acid ester containing small amounts of impurities.

The ratio between the naphthalenedicarboxylic acid and the naphthalenedicarboxylic acid ester obtained above can be controlled by adjusting the alcohol concentration of the alcohol aqueous solution and/or the temperature for the crystallization.

The method of purifying crude naphthalenedicarboxylic acid according to the present invention is very suitable for obtaining a mixture of naphthalenedicarboxylic acid and naphthalenedicarboxylic acid ester having a low content of formylnaphthoic acid from naphthalenedicarboxylic acid containing formylnaphthoic acid as impurity.

In the mixture of the high-purity naphthalenedicarboxylic acid and the naphthalenedicarboxylic acid ester obtained by the method of the invention, the aldehydes are contained in amounts of usually not more than 1,000 ppm, preferably not more than 500 ppm. The high-purity naphthalenedicarboxylic acid is suitably used as a starting material for preparing polyethylene naphthalate. If ethylene glycol is used as the alcohol in the above method and if the resulting mixture of the high-purity naphthalenedicarboxylic acid and the naphthalenedicarboxylic acid ester is subjected to polycondensation reaction by optionally adding ethylene glycol to the mixture, polyethylene naphthalate having a low impurity content can be obtained.

In order to obtain high-purity naphthalenedicarboxylic acid in the invention, the alcohol concentration of the alcohol aqueous solution containing the naphthalenedicarboxylic acid and the naphthalenedicarboxylic acid ester, said solution being obtained after contact of the aldehydes with the sulfite, is lowered to hydrolyze the naphthalenecarboxylic acid ester, and the precipitated naphthalenedicarboxylic acid is recovered.

There is no specific limitation on the way to lower the alcohol concentration, and various ways are available. For example, the alcohol aqueous solution is mixed with water; a part of alcohol is evaporated from the alcohol aqueous solution; or the alcohol aqueous solution is mixed with an alcohol aqueous solution having a lower alcohol concentration.

In the hydrolysis, the alcohol concentration of the alcohol aqueous solution is in the range of usually 5 to 60% by weight, preferably 10 to 40% by weight, more preferably 15 to 30% by weight.

The hydrolysis is carried out under a pressure of usually 2 to 80 kg/cm$^2$, preferably 10 to 50 kg/cm$^2$, at a temperature of usually 160 to 300° C., preferably 200 to 280° C., for a period of usually 0.2 to 6 hours, preferably 1 to 4 hours.

After the hydrolysis is performed, the alcohol aqueous solution is cooled to crystallize (precipitate) the naphthalenedicarboxylic acid. The precipitated naphthalenedicarboxylic acid is separated from the alcohol aqueous solution to obtain high-purity naphthalenedicarboxylic acid.

The method of purifying crude naphthalenedicarboxylic acid to obtain high-purity naphthalenecarboxylic acid according to the invention is very suitable for obtaining naphthalenedicarboxylic acid having a low content of formylnaphthoic acid from naphthalenedicarboxylic acid containing formylnaphthoic acid as impurity.

In the high-purity naphthalenedicarboxylic acid obtained by the method of the invention, the aldehydes are contained in amounts of usually not more than 1,000 ppm, preferably not more than 500 ppm. The high-purity naphthalenedicarboxylic acid is suitably used as a starting material for preparing polyethylene naphthalate.

In the present invention, the method of contact with a sulfite and the method of purification utilizing hydrolysis may be used in combination in order to obtain the mixture of the naphthalenedicarboxylic acid and the naphthalenedicarboxylic acid ester having a low content of formylnaphthoic acid from naphthalenedicarboxylic acid containing formylnaphthoic acid as impurity. When the mixture of the high-purity naphthalenedicarboxylic acid and the naphthalenedicarboxylic acid ester thus obtained is subjected to polycondensation reaction by optionally adding ethylene glycol to the mixture, polyethylene naphthalate having a low impurity content can be obtained.

EFFECT OF THE INVENTION

By the process for preparing polyethylene naphthalate according to the invention, polyethylene naphthalate having a low impurity content can be obtained from crude naphthalenedicarboxylic acid.

By the method of purifying crude naphthalenedicarboxylic acid according to the invention, a mixture of naphthalenedicarboxylic acid and naphthalenedicarboxylic acid ester having a low impurity content or high-purity naphthalenedicarboxylic acid can be obtained.

EXAMPLE

The present invention is further described with reference to the following examples, but it should be construed that the invention is in no way limited to those examples.

Example 1

Into a 1,000 ml autoclave, 100 g of 2,6-naphthalenedicarboxylic acid containing impurities shown in Table 1 (crude NDA), 240 g of ethylene glycol (EG), 160 g of water and 8 g of 0.5% Pd/C particles placed in a vertically movable catalyst basket made of titanium wire netting were introduced. Then, the system was purged with hydrogen to pressurize the system to 3 kg/cm$^2$, and the system was further pressurized to 10 kg/cm$^2$ with nitrogen. During these operations, the catalyst basket was kept in no contact with the solution in the autoclave.

Subsequently, the system was heated at 245° C. for 2 hours, and then the catalyst basket was put down into the solution to contact the catalyst with the solution for 10 minutes.

Thereafter, the autoclave was cooled to 25° C., and the crystals precipitated and the liquid (slurry) were taken out of the autoclave. To the slurry was added 1,000 ml of water, and the crystals were separated from the liquid. Thus, 120 g of the crystals (purified NDA-EG ester mixture) were recovered. The amounts of the impurities contained in the NDA-EG ester mixture are set forth in Table 1.

TABLE 1

| | | Crude NDA | Purified NDA-EG ester mixture |
|---|---|---|---|
| Impurity content (ppm) | Cobalt | 140 | <1 |
| | Manganese | 676 | <1 |
| | Trimellitic acid | 130 | <1 |
| | Formyl-naphthoic acid | 5,590 | 30 |

TABLE 1-continued

| | | Crude NDA | Purified NDA-EG ester mixture |
|---|---|---|---|
| Composition (%) | NDA | 100 | 23 |
| | NDA-mEG | — | 47 |
| | NDA-dEG | — | 25 |
| | Oligomer | — | 5 |

NDA-mGE: monoethylene glycol naphthalenedicarboxylate
NDA-dGE: diethylene glycol naphthalenedicarboxylate Polycondensation Into a glass flask equipped with a simple distillation device, 240 g of the NDA-EG ester mixture was introduced. The glass flask was then immersed in an oil bath at 80° C. and heated to 225° C. over a period of 30 minutes, followed by continuous heating at that temperature. During the heating operation, water distilled from the upper part of the distillation column was recovered. The time at which the distillation of water produced with the progress of esterification reaction ceased was regarded as the time of completion of the esterification.

To the resulting ester-containing composition, a solution obtained by dissolving 21 mg of germanium dioxide as a polymerization catalyst, 15 mg of tetraethylammonium hydroxide as a stabilizer and 39 mg of phosphoric acid in 5 g of ethylene glycol was added.

The ester-containing composition incorporated with the polymerization catalyst and the stabilizer was heated to 260° C., and was stirred for 1 hour with recovering ethylene glycol distilled. Then, the pressure of the reaction system was decreased to not more than 1 Torr with heating the system to 280° C. over a period of 1 hour, whereby ethylene glycol was further distilled. The reaction was continued for another 1.5 hours with distilling ethylene glycol at 280° C. under reduced pressure of not more than 1 Torr. Thereafter, the reaction was terminated, and the produced polyethylene naphthalate was recovered.

The results of measurements of the intrinsic viscosity (measured in o-chlorophenol/phenol solution at 25° C., o-chlorophenol:phenol=1:1), glass transition temperature (Tg, measured by a differential scanning calorimeter), melting point (Tm) and hue (L, a and b, measured by a color tester) of the polyethylene naphthalate are set forth in Table 2.

Comparative Example 1

A NDA-EG ester mixture was prepared in the same manner as in Example 1, except that the purge of the autoclave with hydrogen was not performed and the 0.5% Pd/C particles were not introduced. Using the NDA-EG ester mixture, polyethylene naphthalate was prepared in the same manner as in Example 1. The results are set forth in Table 2.

TABLE 2

| | Ex. 1 | Comp. Ex. 1 |
|---|---|---|
| Intrinsic viscosity (dl/g) | 0.55 | 0.55 |
| Tg (° C.) | 116 | 115 |
| Tm (° C.) | 266 | 263 |

TABLE 2-continued

| | Ex. 1 | Comp. Ex. 1 |
|---|---|---|
| Hue | | |
| L | 58 | 49 |
| a | −1.3 | 2.3 |
| b | −5.3 | 20.5 |

Example 2

Esterification Step

Into a 50 ml autoclave, 2 g of 2,6-naphthalenedicarboxylic acid containing 2,100 ppm of 6-formyl-2-naphthoic acid, 6.5 g of ethylene glycol and 3.5 g of water were introduced. Then, the system was purged with nitrogen to pressurize the system to 5 kg/cm$^2$, and was heated at 250° C. for 3 hours, followed by cooling the autoclave. By these operations, the 2,6-naphthalenedicarboxylic acid was esterified for the most part and turned into a mixture containing a monoester and a diester. The results of composition analysis of the mixture are set forth in Table 3.

TABLE 3

| Composition | Amount |
|---|---|
| NDA | 21.2% by mol |
| NDA-monoEG ester | 48.2% by mol |
| NDA-diEG ester | 28.9% by mol |
| NDA-DEG ester | 0.3% by mol |
| Oligomer | 1.4% by mol |

DEG: diethylene glycol

Formation of 6-Formyl-2-Naphthoic Acid Adduct

Subsequently, a solution obtained by dissolving 0.5 g of sodium hydrogensulfite in an ethylene glycol aqueous solution (EG: 6.5 g, water: 3.5 g) was introduced into the autoclave. Then, the system was purged with nitrogen again to pressurize the system to 5 kg/cm$^2$, and was heated at 150° C. for 0.5 hour, followed by cooling the autoclave.

Crystallization of NDA

The reaction solution obtained by the above reaction was poured into 50 ml of distilled water, and they were stirred for several minutes. The resulting mixture was separated into crystals and a liquid by filtration. The crystals were then washed with 30 ml of distilled water and dried for one day. Thus, 2.2 g of crystals (a mixture of 2,6-naphthalenedicarboxylic acid and 2,6-naphthalenedicarboxylic acid ester) were recovered. The content of the 6-formyl-2-naphthoic acid in the crystals was 360 ppm.

Comparative Example 2

Purification of crude 2,6-naphthalenedicarboxylic acid was carried out in the same manner as in Example 2, except that no sodium hydrogensulfite was introduced into the autoclave. The content of the 6-formyl-2-naphthoic acid in the resulting crystals of the mixture of 2,6-naphthalenedicarboxylic acid and 2,6-naphthalenedicarboxylic acid ester was 2,000 ppm.

Example 3

Esterification Step

Into a 50 ml autoclave, 2 g of 2,6-naphthalenedicarboxylic acid containing 2,100 ppm of 6-formyl-2-naphthoic acid, 6 g of methanol and 4 g of water were introduced. Then, the system was purged with nitrogen to pressurize the system to 5 kg/cm², and was heated at 250° C. for 3 hours, followed by cooling the autoclave. By these operations, the 2,6-naphthalenedicarboxylic acid was esterified for the most part and turned into a mixture containing a monoester and a diester. The results of composition analysis of the mixture are set forth in Table 4.

TABLE 4

| Composition | Amount |
| --- | --- |
| NDA | 45.7% by mol |
| NDA-mono ester | 29.1% by mol |
| NDA-di ester | 27.3% by mol |

Formation of 6-Formyl-2-Naphthoic Acid Adduct

Subsequently, a solution obtained by dissolving 0.2 g of sodium hydrogensulfite in a methanol aqueous solution (methanol: 6 g, water: 4 g) was introduced into the autoclave. Then, the system was purged with nitrogen again to pressurize the system to 5 kg/cm², and was heated at 250° C. for 0.1 hour. Thereafter, the autoclave was cooled to 25° C. over a period of 75 minutes Crystallization of NDA The reaction solution obtained by the above reaction was poured into 50 ml of distilled water, and they were stirred for several minutes. The resulting mixture was separated into crystals and a liquid by filtration. The crystals were then washed with 30 ml of distilled water and dried for one day. Thus, 2.2 g of crystals (a mixture of 2,6-naphthalenedicarboxylic acid and 2,6-naphthalenedicarboxylic acid ester) were recovered. The content of the 6-formyl-2-naphthoic acid in the crystals was 1,087 ppm.

What is claimed is:

1. A process for preparing polyethylene naphthalate, comprising the steps of:

mixing crude naphthalenedicarboxylic acid and an ethylene glycol aqueous solution, heating the resulting mixture to esterify a part of the naphthalenedicarboxylic acid and thereby give a naphthalenedicarboxylic acid ester and dissolving the naphthalenedicarboxylic acid ester in the ethylene glycol aqueous solution;

then contacting impurities, which are contained in the crude naphthalenedicarboxylic acid and capable of being hydrogenated, with hydrogen in the presence of a hydrogenation catalyst to hydrogenate the impurities and dissolving the hydrogenated impurities in the ethylene glycol aqueous solution; and subsequently crystallizing the naphthalenedicarboxylic acid ester, separating the resulting crystals from the ethylene glycol aqueous solution and polycondensing the resulting naphthalenedicarboxylic acid ester.

2. The process for preparing polyethylene naphthalate as claimed in claim 1, wherein the ethylene glycol aqueous solution for esterifying the crude naphthalenedicarboxylic acid has an ethylene glycol concentration of 20 to 95% by weight based on 100% by weight of the total of water and ethylene glycol.

3. A method of purifying crude naphthalenedicarboxylic acid, comprising the steps of:

mixing crude naphthalenedicarboxylic acid and an alcohol aqueous solution, heating the resulting mixture to esterify a part of the naphthalenedicarboxylic acid and thereby give a naphthalenedicarboxylic acid ester and dissolving the naphthalenedicarboxylic acid ester in the alcohol aqueous solution;

then contacting aldehydes, which are contained in the crude naphthalenedicarboxylic acid, with a sulfite to give aldehyde adducts and dissolving the aldehyde adducts in the alcohol aqueous solution; and subsequently crystallizing the naphthalenedicarboxylic acid and the naphthalenedicarboxylic acid ester and separating them from the alcohol aqueous solution.

4. The method of purifying crude naphthalenedicarboxylic acid as claimed in claim 3, wherein the alcohol is methanol, ethanol or ethylene glycol.

5. The method of purifying crude naphthalenedicarboxylic acid as claimed in claim 3, wherein the crude naphthalenedicarboxylic acid is naphthalenedicarboxylic acid containing formylnaphthoic acid.

6. A process for preparing polyethylene naphthalate, comprising the steps of:

mixing crude naphthalenedicarboxylic acid and an ethylene glycol aqueous solution, heating the resulting mixture to esterify a part of the naphthalenedicarboxylic acid and thereby give a naphthalenedicarboxylic acid ester and dissolving the naphthalenedicarboxylic acid ester in the ethylene glycol aqueous solution;

then contacting aldehydes, which are contained in the crude naphthalenedicarboxylic acid, with a sulfite to give aldehyde adducts and dissolving the aldehyde adducts in the ethylene glycol aqueous solution; and subsequently crystallizing the naphthalenedicarboxylic acid ester, separating the resulting crystals from the ethylene glycol aqueous solution and polycondensing the resulting naphthalenedicarboxylic acid ester.

7. A method of purifying crude naphthalenedicarboxylic acid, comprising the steps of:

mixing crude naphthalenedicarboxylic acid and an alcohol aqueous solution, heating the resulting mixture to esterify a part of the naphthalenedicarboxylic acid and thereby give a naphthalenedicarboxylic acid ester and dissolving the naphthalenedicarboxylic acid ester in the alcohol aqueous solution;

then contacting aldehydes, which are contained in the crude naphthalenedicarboxylic acid, with a sulfite to give aldehyde adducts and dissolving the aldehyde adducts in the alcohol aqueous solution; and subsequently lowering the alcohol concentration of the alcohol aqueous solution to hydrolyze the naphthalenedicarboxylic acid ester and recovering the naphthalenedicarboxylic acid.

8. The method of purifying crude naphthalenedicarboxylic acid as claimed in claim 7, wherein the alcohol is methanol, ethanol or ethylene glycol.

9. The method of purifying crude naphthalenedicarboxylic acid as claimed in claim 7, wherein the crude naphthalenedicarboxylic acid is naphthalenedicarboxylic acid containing formylnaphthoic acid.

* * * * *